United States Patent
Veldman et al.

(10) Patent No.: US 8,388,658 B2
(45) Date of Patent: Mar. 5, 2013

(54) DYNAMIC SPINAL STABILIZATION ASSEMBLY WITH SLIDING COLLARS

(75) Inventors: Michael S. Veldman, Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/217,653

(22) Filed: Aug. 25, 2011

(65) Prior Publication Data

US 2011/0307017 A1 Dec. 15, 2011

Related U.S. Application Data

(63) Continuation of application No. 11/668,792, filed on Jan. 30, 2007, now Pat. No. 8,029,547.

(51) Int. Cl.
*A61B 17/70* (2006.01)
(52) U.S. Cl. ........................................................ 606/254
(58) Field of Classification Search .................. 606/246, 606/253–279; 428/188
See application file for complete search history.

(56) References Cited

U.S. PATENT DOCUMENTS

| 4,745,913 | A | * | 5/1988 | Castaman et al. | 606/59 |
| 5,042,982 | A | * | 8/1991 | Harms et al. | 606/256 |
| 5,176,679 | A | * | 1/1993 | Lin | 606/272 |
| 5,409,488 | A | * | 4/1995 | Ulrich | 606/260 |
| 5,466,238 | A | * | 11/1995 | Lin | 606/264 |
| 5,562,660 | A | * | 10/1996 | Grob | 606/258 |
| 5,944,719 | A | * | 8/1999 | Leban | 606/59 |
| 7,951,170 | B2 | * | 5/2011 | Jackson | 606/257 |
| 2003/0220643 | A1 | * | 11/2003 | Ferree | 606/61 |
| 2005/0131407 | A1 | * | 6/2005 | Sicvol et al. | 606/61 |
| 2005/0182401 | A1 | * | 8/2005 | Timm et al. | 606/61 |
| 2005/0203517 | A1 | * | 9/2005 | Jahng et al. | 606/61 |
| 2007/0093813 | A1 | * | 4/2007 | Callahan et al. | 606/61 |
| 2007/0233075 | A1 | * | 10/2007 | Dawson | 606/61 |

* cited by examiner

*Primary Examiner* — Eduardo C Robert
*Assistant Examiner* — Steven Cotroneo

(57) ABSTRACT

A dynamic spinal stabilization assembly includes a rod having a plurality of slidable collars thereon. The rod is mounted to at least one of the relevant bone anchoring element(s) via the collars. The collars are spaced from one another such that the bone anchoring element engages at least two collars. The collars may be arranged on the rod so that adjacent collars are longitudinally spaced from one another by a distance not more than one-half the length of the rod-receiving channel in the relevant bone anchoring element. There may be elastic elements slidably disposed on the rod between adjacent collars.

20 Claims, 10 Drawing Sheets

DYNAMIC SPINAL STABILIZATION ASSEMBLY WITH SLIDING COLLARS

REFERENCE TO RELATED APPLICATIONS

This application is a continuation of U.S. patent application No. 11/668,792, filed Jan. 30, 2007, now allowed, the contents of which is hereby incorporated by reference herein in its entirety.

BACKGROUND

The present invention relates to spinal stabilization, and more particularly to dynamic spinal stabilization.

Numerous systems have been developed for stabilizing the vertebral column so as to promote healing, reduce pain, and/or allow for spinal fusion. Typical systems involve anchor members (e.g., polyaxial screws) secured to consecutive vertebrae, with a spinal rod rigidly fixed to the anchor members. The anchor members are typically screwed into the posterior portions of the vertebrae and pass through the pedicles and a substantial portion of the vertebral bodies and therefore provide a fixed and durable connection. The spinal rods are then clamped to the anchor members in a conventional fashion, creating a rigid stabilization structure. In most situations, one such structure is provided on each lateral side of the spine.

While such structures hold the vertebrae correctly positioned relative to each other, they tend to considerably stiffen the spine. This may significantly limit the patient's post-operative freedom of movement and/or may lead to undesirable loadings on nearby vertebrae. Accordingly, efforts have been made to develop stabilization approaches that can tolerate some movement, with the resulting systems typically referred to as dynamic spinal stabilization systems. Examples of dynamic stabilization systems are shown in U.S. Pat. No. 5,672,175 to Martin and U.S. Patent Application Publication No. 2005/0171540 to Lim et al.

While the prior art dynamic spinal stabilization systems, such as the Martin and Lim et al. systems, allow for dynamic spinal stabilization, they may not be entirely satisfactory in some situations. Thus, there remains a need for alternative approaches to dynamic spinal stabilization, advantageously approaches that allow for easy installation while remaining robust in use.

SUMMARY

A dynamic spinal stabilization assembly according to one embodiment comprises a rod having a plurality of slidable collars thereon. The rod is mounted to at least one of the relevant bone anchoring element(s) via the collars. The collars are spaced from one another such that the bone anchoring element engages at least two collars.

In one illustrative embodiment, an assembly for dynamic stabilization of a spine comprises: a first bone anchoring element having a first bone engaging section extending along a first axis and a first coupling section; the first coupling section having a first longitudinal channel of at least a first length extending generally transverse to the first axis; a second bone anchoring element spaced from the first bone anchoring element and optionally having a similar channel; an elongate rod; a plurality of mounting collars slidable along the rod and spaced from one another by a distance not exceeding the first length; the rod slidably mounted to the first bone anchoring element via at least two of the collars and supported by the second bone anchoring element. The assembly may advantageously further comprise a plurality of elastic elements disposed about the rod between adjacent ones of the collars; and, the collars and the elastic elements, in combination, may substantially longitudinally cover the rod.

Other aspects of various embodiments of the inventive apparatus and related methods are also disclosed in the following description. The various aspects may be used alone or in any combination, as is desired.

DETAILED DESCRIPTION

Figure 1:
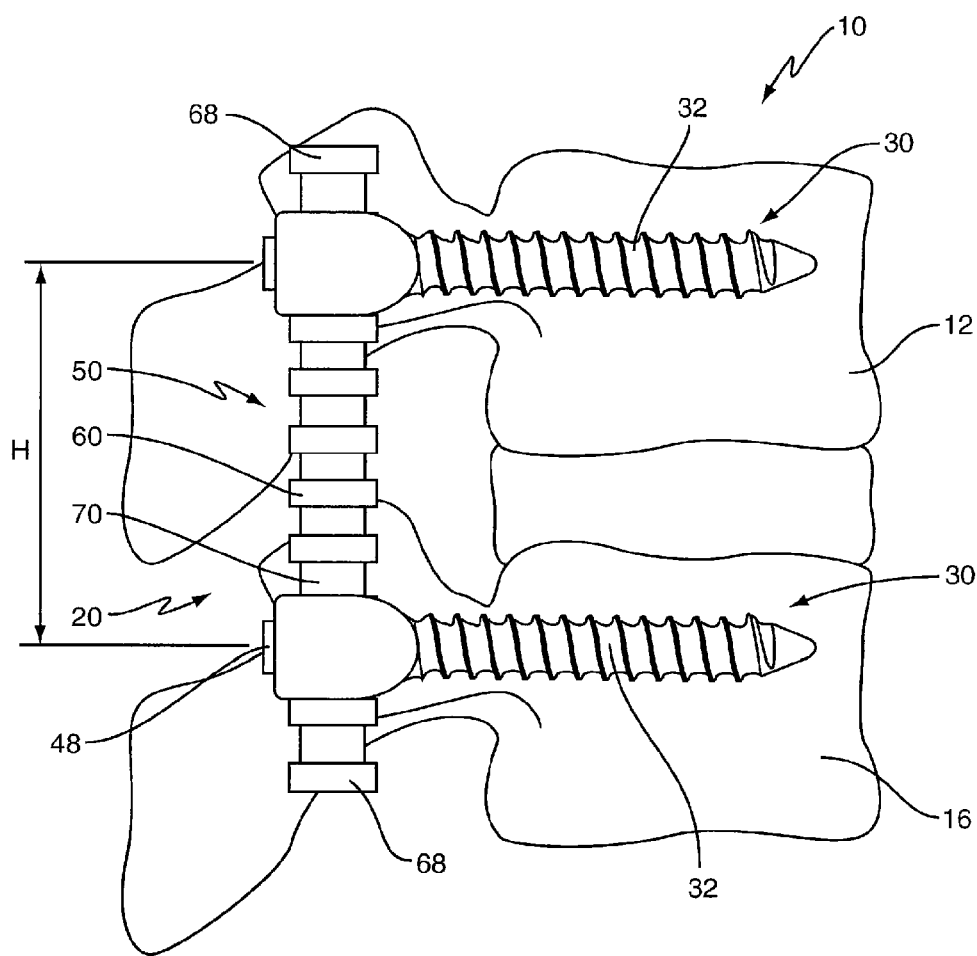
FIG. 1 shows one embodiment of a dynamic spinal stabilization assembly secured to a spinal column, with the spinal column in the neutral position.
Figure 2:
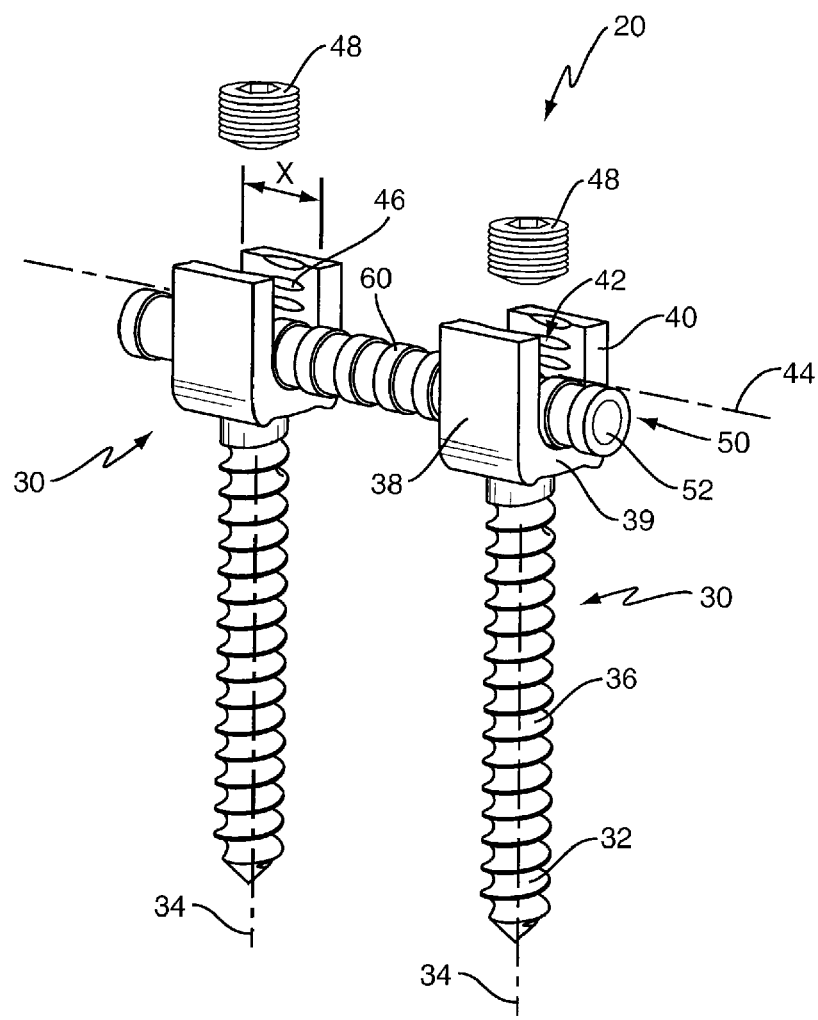
FIG. 2 shows a perspective partially exploded view of the dynamic spinal stabilization assembly of FIG. 1.

A dynamic spinal stabilization assembly 20 according to one embodiment is shown in FIG. 1, and generally indicated at 20. For simplicity, FIG. 1 shows the dynamic spinal stabilization assembly 20 being used to dynamically stabilize two adjacent vertebrae, a superior vertebra 12 and an inferior vertebra 16, in a spinal column 10. The dynamic spinal stabilization assembly 20 of FIG. 1 includes two or more bone anchoring elements 30 and a rod assembly 50. For simplicity, the bone anchoring elements 30 of FIG. 1 take the form of monolithic monoaxial screws, and are therefore sometimes referred to herein as bone screws 30. However, it should be understood that other forms of anchoring elements may be used, such as pedicle hooks, more complex polyaxial pedicle screws, closed-headed bone screw assemblies, offset connectors, or the like, or combinations thereof. Referring to FIG. 2, each bone screw 30 includes a bone engaging section 32, a head section 38, and a locking element 48. The bone engaging section 32 engages the relevant vertebra 12,16 in a fashion well known in the art of pedicle screws. For example, the bone engaging section 32 is typically formed as a straight shank 32 extending along axis 34 with suitable external threads 36 for engaging bone. The head section 38 is joined to shank 32 and receives and supports the rod assembly 50. The head section 38 typically includes a base section 39 proximate the shank 32 and two upstanding arms 40 that together help define an open-topped transverse channel 42 of length X along its axis 44. When the dynamic spinal stabilization assembly 20 is assembled, the rod assembly 50 rests in this channel 42. Accordingly, the channel 42 may, if desired, include ribs, protrusions, or other alignment features to aid in keeping the collars 60 (discussed below) properly aligned. The interior of the upper portion of arms 40 advantageously includes threads 46 or other means for engaging the locking member 48. The locking member 48 may take any form known in the art, but typically takes the form of a simple exteriorly threaded setscrew. Advancing the locking member 48 toward the shank 32 allows the rod assembly 50 to be clamped to the bone screw 30 between the locking member 48 and the base portion 39 of head section 38. If desired, optional suitable press plates or similar structures (not shown) may be disposed both above and below the rod assembly 50 when it is in channel 42; these press plates may be associated with the head section 38, the locking element 48, or distinct therefrom.

Figure 3:
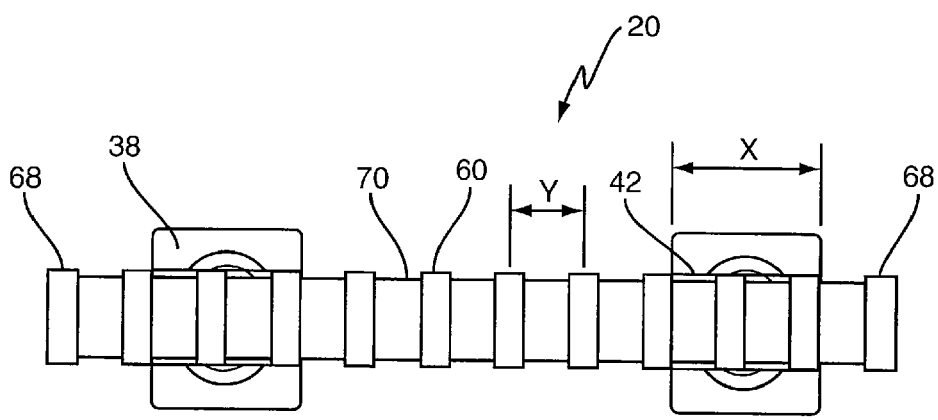
FIG. 3 shows a top view of the dynamic spinal stabilization assembly of FIG. 2 with locking elements removed for clarity.
Figure 4:
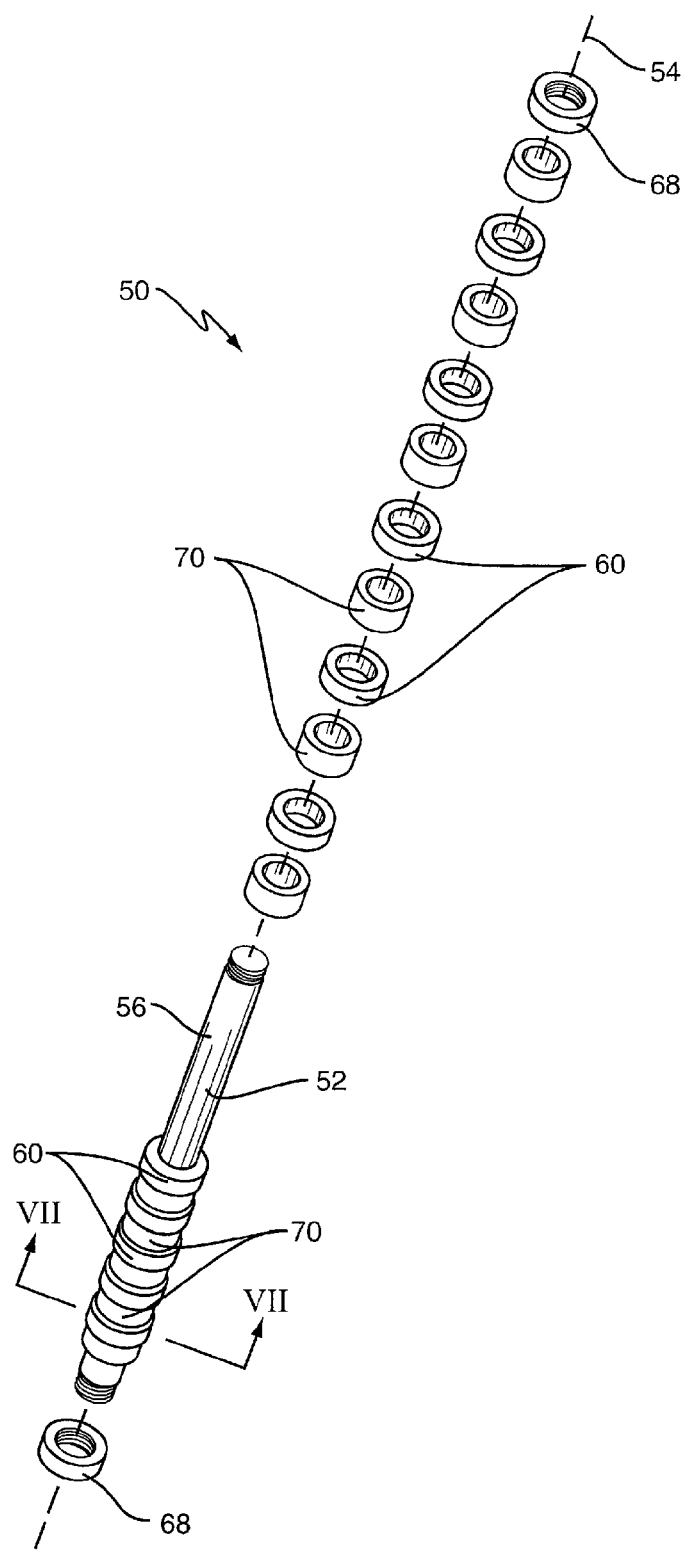
FIG. 4 shows a partially exploded view of a rod assembly.
Figure 5:
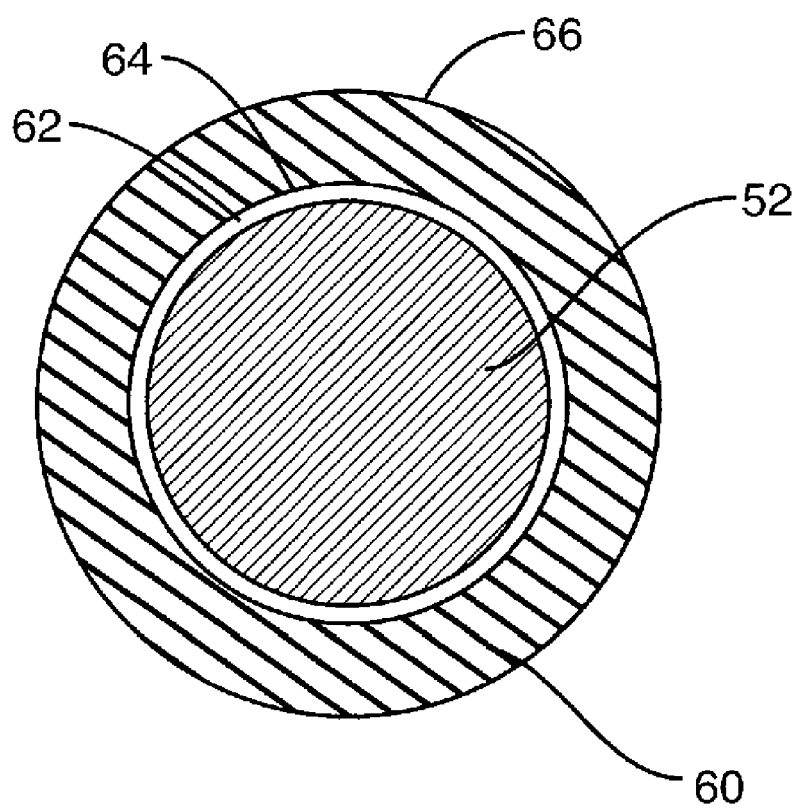
FIG. 5 shows a rod assembly cross section taken through a collar along line VII-VII in FIG. 4.

Referring to FIGS. 3-4, the rod assembly 50 includes a spinal rod 52, a plurality of collars 60, a plurality of elastic elements 70, and a pair of end stops 68. The spinal rod 52 is an elongate body, typically cylindrical in shape that extends along a longitudinal axis 54. Of course, the rod 52 may take other forms known in the art of spinal rods, such as having an elliptical cross-section, etc. Because the rod 52 is expected to carry significant loads, the rod 52 may be made from a suitably strong rigid material known in the art, such as titanium or semi-rigid material such as PEEK, polyurethane, polypropylene, or polyethylene.

Figure 6A:
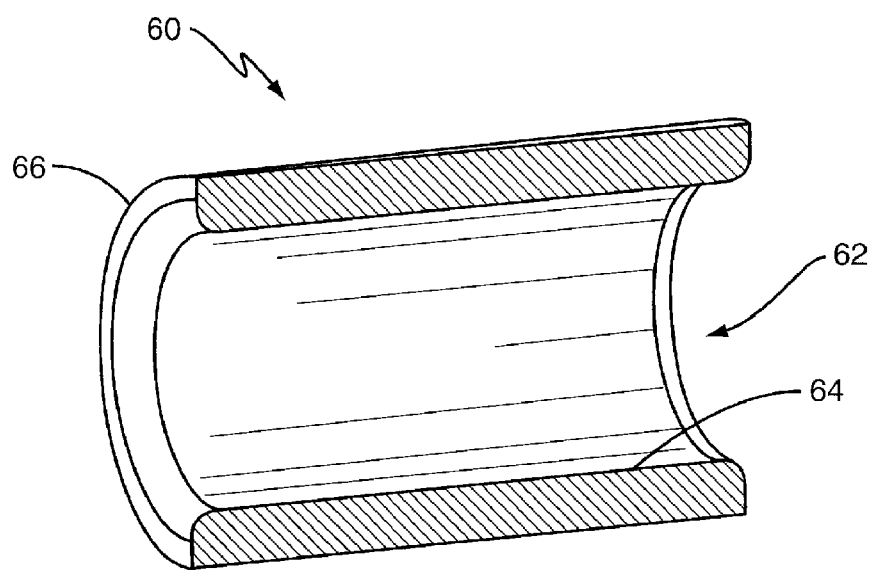
FIGS. 6A-6B show longitudinal cross-sections of various collar embodiments.
Figure 6B:
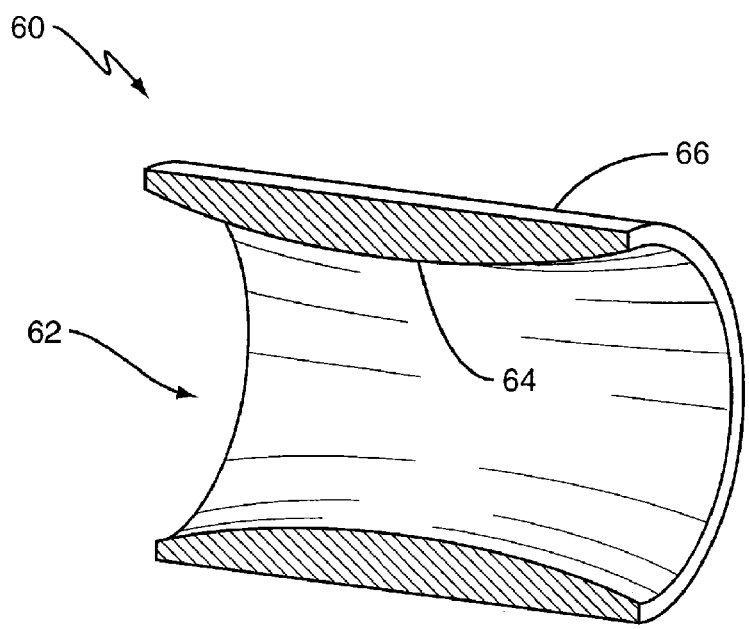

The collars 60 are slidably disposed on the rod 52 in spaced relation to each other, and are advantageously substantially identical. The collars 60 are generally annular bodies with a central bore 62 defined by an interior surface 64 that faces rod 52. The interior surface 64 of collars 60 is advantageously contoured to facilitate assembly and to inhibit binding which might negatively affect the desired sliding motion. Thus, referring to FIG. 6A, the entries to the otherwise cylindrically profiled central bore 62 may advantageously be generously radiused. Alternatively, referring to FIG. 6B, the profile of the interior surface 64 may be continuously curved so that a minimum inner diameter is present proximate the center of the collar 60. Regardless, bore 62, at its smallest point, should be sized just slightly larger than the rod 52 so that a sliding fit is established therebetween without undue clearance. The collars 60 should be of sufficient strength to withstand the expected clamping forces required to mate the rod assembly 50 to the bone anchoring elements 30. Therefore, the collars 60 should be formed of a suitably strong material such as titanium, stainless steel, cobalt chromium, ceramic, or the like. Further, the exterior surface 66 of the collars 60 should be relatively hard, and the collar 60 should have sufficient wall thickness to withstand the expected loadings. The collar interior surface 64 may likewise be relatively hard or may be coated with, or otherwise formed with a suitable friction reducing material. For example, the collar interior surface 64 may be coated with low friction material (e.g., a ceramic or low friction polymer), and/or finished in a suitable manner, to reduce any friction between the collar 60 and the exterior surface 56 of rod 52. Alternatively, or additionally, the exterior surface 56 of rod 52 may likewise be coated and/or finished.

Referring again to FIGS. 3-4, an elastic element 70 is disposed between each pair of adjacent collars 60, and advantageously between the terminal collars 60 and the end stops 68. In some embodiments, the elastic elements 70 may take the form of simple coil springs disposed about rod 52. Alternatively, the elastic elements 70 may advantageously take the form of annular bodies of elastomeric material, such as polycarbonate urethane. These elastic elements 70, or bumpers, should be able to undergo compression and resiliently return to their natural state upon removal of the corresponding load.

The bumpers 70 may advantageously be sized to be radially slightly smaller than the collars 60, with any appropriate longitudinal length. The end faces of the bumpers 70 are advantageously complementary in shape to the surfaces they abut against. Thus, if the collars 60 have longitudinal end faces that are concave, the endfaces of the bumpers 70 are advantageously complementarily convex, and vice versa.

The end stops 68 are secured to, or may be formed by, the superior and inferior ends of rod 52. These stops may take any form known in the art, such as a simple enlarged cap that is threaded onto the respective rod 52 end. See FIG. 4. The end stops 68 function to prevent the collars 60 and bumpers 70 from longitudinally moving off the ends of rod 52. In addition, the end stops 68 help limit the overall movement of the spinal segment being stabilized.

The bumpers 70 help space the adjacent collars 60 from one another. Advantageously, adjacent collars 60 are spaced from one another by a distance Y that is less than distance X representing the length of the rod-receiving channel 42 in bone screw head section 38. See FIG. 3. Advantageously, distance Y is one-half or less than distance X. Because spacing Y is less than channel length X, at least two collars 60 are present in each channel 42 when the dynamic spinal stabilization assembly 20 is finally assembled. Accordingly, when locking element 48 is advanced toward shank 32, at least two collars 60 are engaged (e.g., clamped) at the corresponding bone screw 30. Because two collars 60 are acting as the interface between the bone screw 30 and the rod 52 at the clamping location, rather than a single collar, the rod 52 may be held in a desired alignment more easily. Further, for the embodiment of FIGS. 1-4, the surgeon need not be concerned about where the bone screws 30 and collars 60 will be located along the rod assembly 50, because the bone screw 30 will be able to engage at least two collars 60 no matter what its longitudinal position is along the rod assembly 50.

Figure 7:
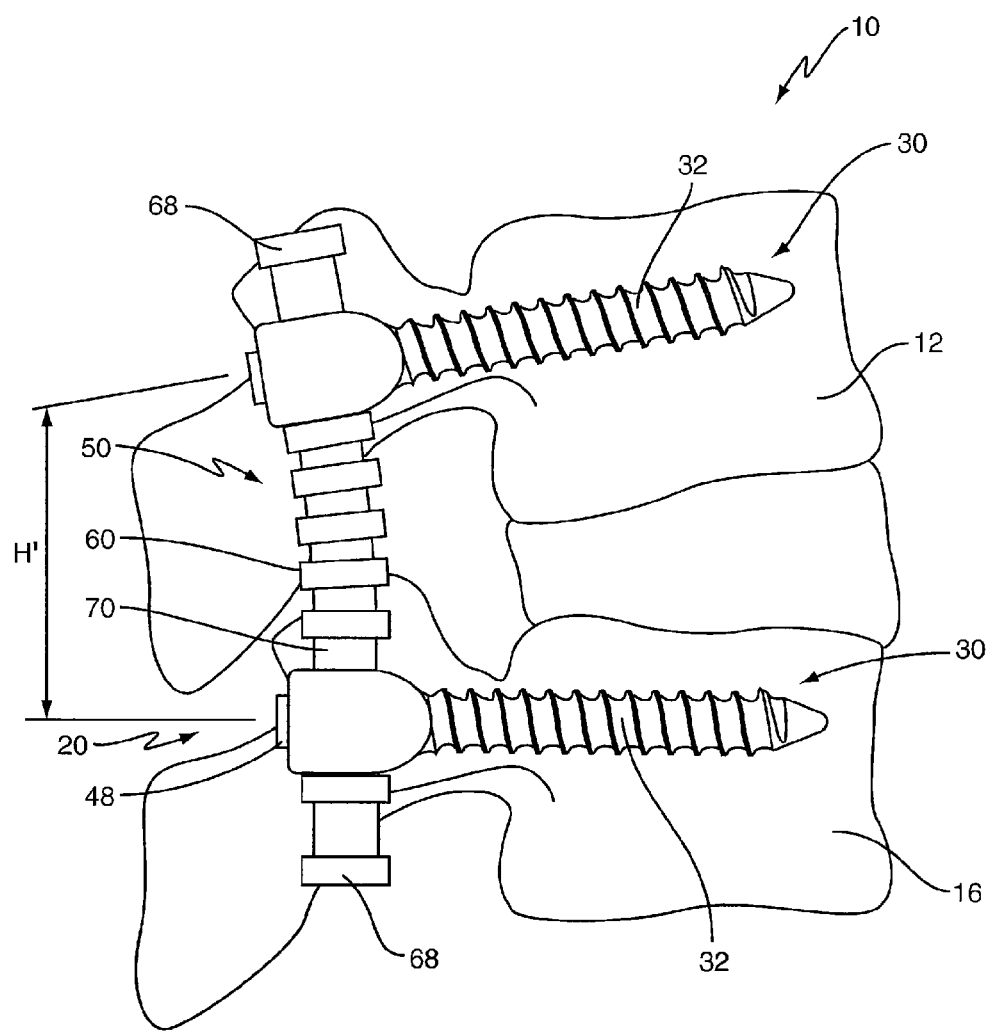
FIG. 7 shows the dynamic spinal stabilization assembly of FIG. 1 with the spinal column undergoing extension.
Figure 8:
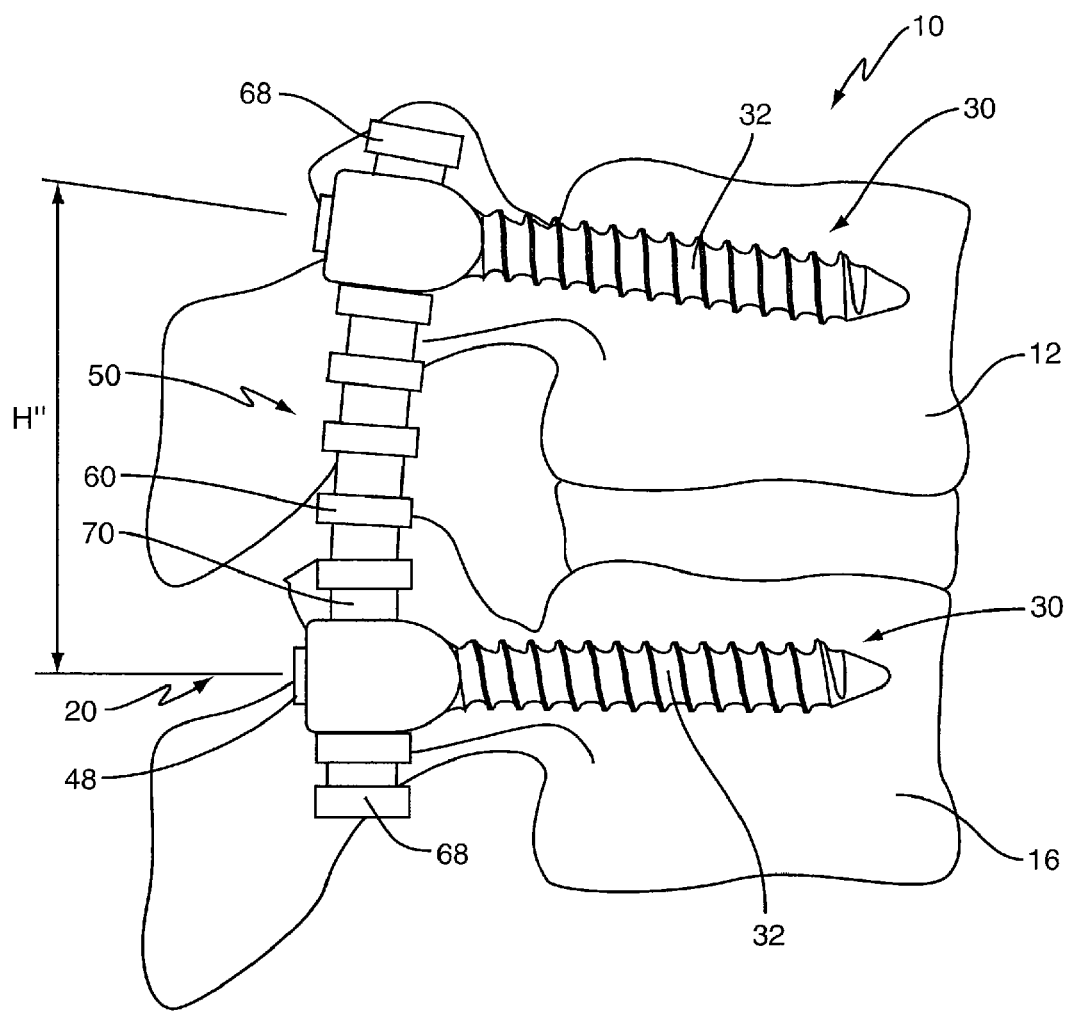
FIG. 8 shows the dynamic spinal stabilization assembly of FIG. 1 with the spinal column undergoing flexion.

Because the rod 52 is slidably coupled to the bone screws 30, via the sliding collars 60, the bone screws 30 are allowed to move longitudinally toward or away from each other along the rod 52, rather than being held in a fixed relative relationship. For example, the bone screws in FIG. 1 are spaced from one another by distance H. When the spinal column 10 undergoes extension, the bone screws 30 will have a tendency to move toward each other, shortening the distance to H' as shown in FIG. 7. Such movement is allowed by the sliding coupling between the rod 52 and the bone screws 30, and will tend to compress the "stack" of collars 60 and elastic elements 70 present between the bone screws 30. Thus, the elastic elements 70 provide a resistance to, and dampening of, the relative compression between the bone screws 30. When the spinal column 10 is subsequently returned to its normal position, the elastic elements 70 in the stack expand back to their "normal" state. Likewise, the bone screws 30 have a tendency to move away from each other when the spinal column 10 undergoes flexion, lengthening the distance to H" as shown in FIG. 8. As can be seen in FIG. 8, the more superior and inferior elastic elements 70, i.e., those disposed superiorly to the superior bone screw 30 and inferior to the inferior bone screw 30, are compressed between the respective bone screw 30 and the respective end stop 68 when the spinal column 10 undergoes flexion. Thus, the elastic elements 70 help space the collars 60 from one another during assembly, and then act to elastically resist/dampen movement of the rod 52 relative to the bone screws 30 after assembly.

The dynamic spinal stabilization assembly 20 may be installed during a surgical procedure. The surgical site is prepared in a conventional fashion, and the spinal column 10 is approached via a posterior and/or lateral approach. If desired, a minimally invasive technique may be used, such as that discussed in U.S. Patent Application Publication No. 2005/0171540, which is incorporated herein by reference. Once the bone screws 30 are installed into the respective vertebrae, the rod assembly 50 may be inserted into the channels 42 such that at least two collars 60 are present in each channel 42. The locking elements 48 are then tightened so as to slidably secure the rod 52 to the bone screws 30. The surgical procedure then proceeds in a conventional fashion.

In the embodiments above, the rod assembly 50 included a plurality of elastic elements 70, with a single elastic element 70 disposed between each pair of adjacent collars 60 (or a collar 60 and an end stop 68). However, in some embodiments, there may be multiple elastic elements 70 between each pair of adjacent collars 60. Further, the discussion above has assumed that the collars 60 are uniformly spaced from one another prior to installation. While believed to be advantageous, such is not required, and the collars 60 may be unevenly spaced from one another, provided that they are properly spaced.

Figure 9:
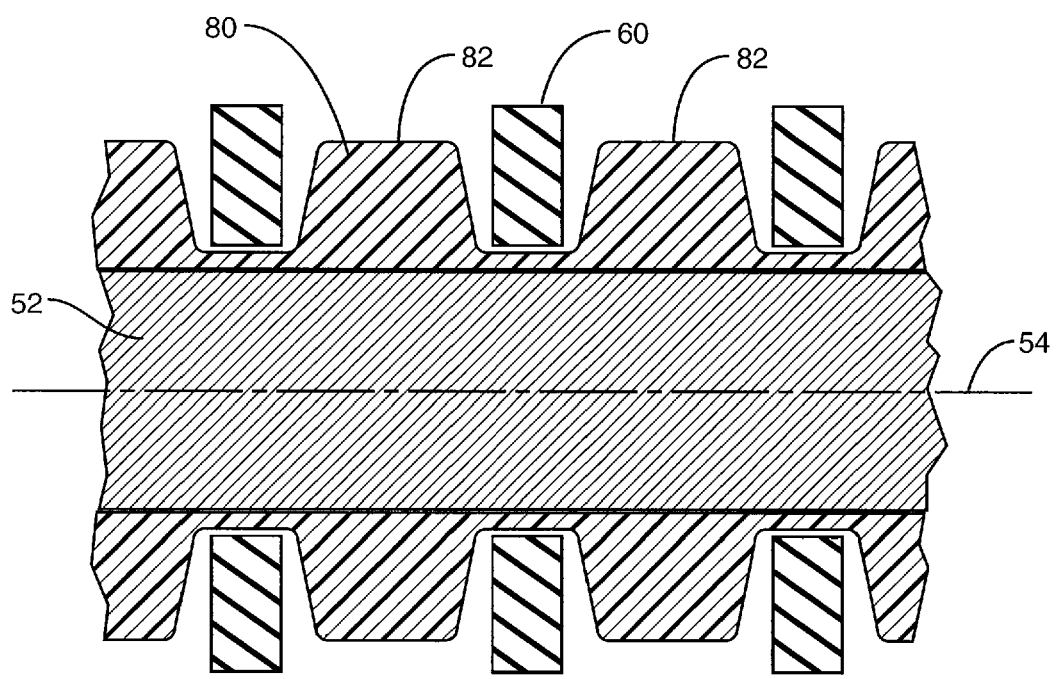
FIG. 9 shows a partial sectional view of an alternative embodiment of a rod assembly that utilizes a sleeve over the rod to help maintain a plurality of collars in position.

Conversely, in some embodiments, all or some of the plurality of elastic elements 70 may be replaced with a single elastic element. For example, the embodiment of FIG. 9 employs an elastomeric sleeve 80 disposed around the rod 52, with the sleeve 80 having a plurality of spaced apart protrusions 82 that function as bumpers 70. Each collar 60 may be positioned between adjacent protrusions 82, with the protrusions 82 acting to keep the collars 60 spaced from one another. Such a sleeve 80 could be assembled with the collars 60, and then slid over the rod 52, if desired. In an alternative embodiment, the sleeve 80 may be disposed around the exterior of the collars 60. Further, if the sleeve is sufficiently elastic and "radially" stretched over the collars 60, the protrusions 82 may not be necessary on such an exteriorly disposed sleeve in order to help hold the collars 60 in spaced relation during assembly.

The discussion above has also assumed a cylindrical exterior shape for the collars 60 and bumpers 70; however, such is not required in all embodiments. Indeed, the collars 60 and bumpers 70 may alternatively be faceted, such as square, rectangular, or hexagonal, or may have any other desired exterior shape or combination of shapes. And, it should be noted that neither all the collars 60 nor all the bumpers 70 need be of a uniform longitudinal length. Further still, in some embodiments, the collars 60 are freely rotatable about the rod longitudinal axis 54; in other embodiments, the collars 60 may be constrained against such rotation. For example, the rod 52 may have a non-circular cross section, with the bore 62 of the collars 60 having a corresponding shape. The non-circular cross-section may be any appropriate shape (e.g., square or otherwise faceted, D-shaped, etc.) and/or may include longitudinally running ribs/channels, as is desired.

In the discussion above, it has been assumed that the bumpers 70 abut the adjacent collars 60/end stop 68 without being affixed thereto. As such, the bumpers 70 are resistive to a compressive load thereon, but not to a tensile force. However, in some embodiments, the bumpers 70 may be attached to, interlocked with, or formed with the adjacent collars 60/end stop 68. With such an arrangement, the bumper 70 is also able to resist tensile loads between the relevant collars 60/end stop 68. Alternatively, or in addition thereto, gaps may be present between all or some of the bumpers 70 and the adjacent collars 60 and/or end stops 68 in some embodiments, which allows for some relatively unrestricted motion before the dampening of the bumpers 70 starts.

Figure 10:
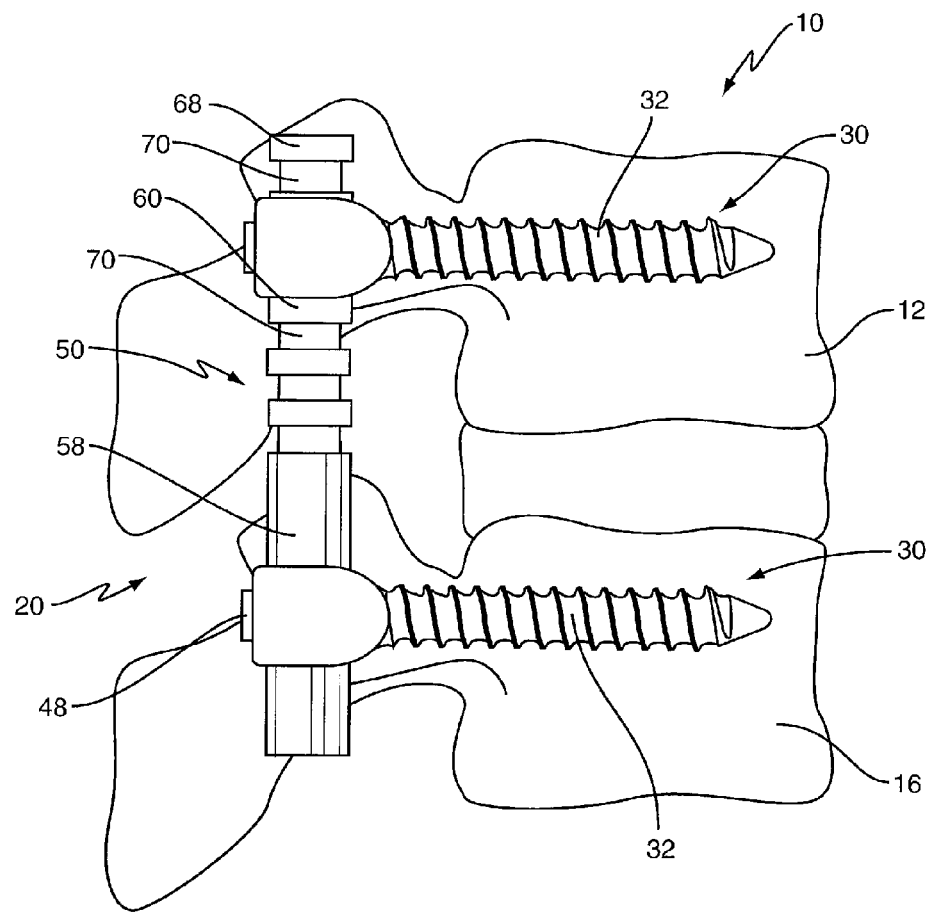
FIG. 10 shows an alternative embodiment of a dynamic spinal stabilization assembly with the rod mounted fixedly at one location and slidably at another.

The rod assembly 50 of FIGS. 1-4 is slidingly secured to each bone screw 30 via corresponding collars 60; however this is not required in all embodiments. In some embodiments, the rod assembly 50 may be secured slidingly to some bone screws 30 and non-slidingly to other bone screws 30. For example, as shown in FIG. 10, a section 58 of rod 50 may be made relatively larger, such as large as the exterior surface of collars 60, with this "fat" section 58 clamped to a bone screw to form a non-sliding connection. Such is one example of a rod assembly 50 that is fixedly mounted to a given bone screw 30, while still allowing a slidable mounting to the other bone screws via collars 60. Alternatively, some collars 60 may have means associated therewith to selectively disable their sliding ability, such as by having setscrews (not shown) that may be moved to a locking position against the rod 52 to disable the sliding motion of the corresponding collar. Further, there may be sections of the rod 52 where neither collars 60 nor bumpers 70 are present, and clamping may take place in these sections or at other locations.

As can be appreciated, the rod 52 need not be straight; indeed, a pre-bent rod may be used. If the amount of rod bending is significant, it may be advantageous for the bore 62 to be tapered to accommodate the bend in the rod 52. For such situations, the longitudinal axis 54 of the rod 52 is not a straight line.

Figure 11:
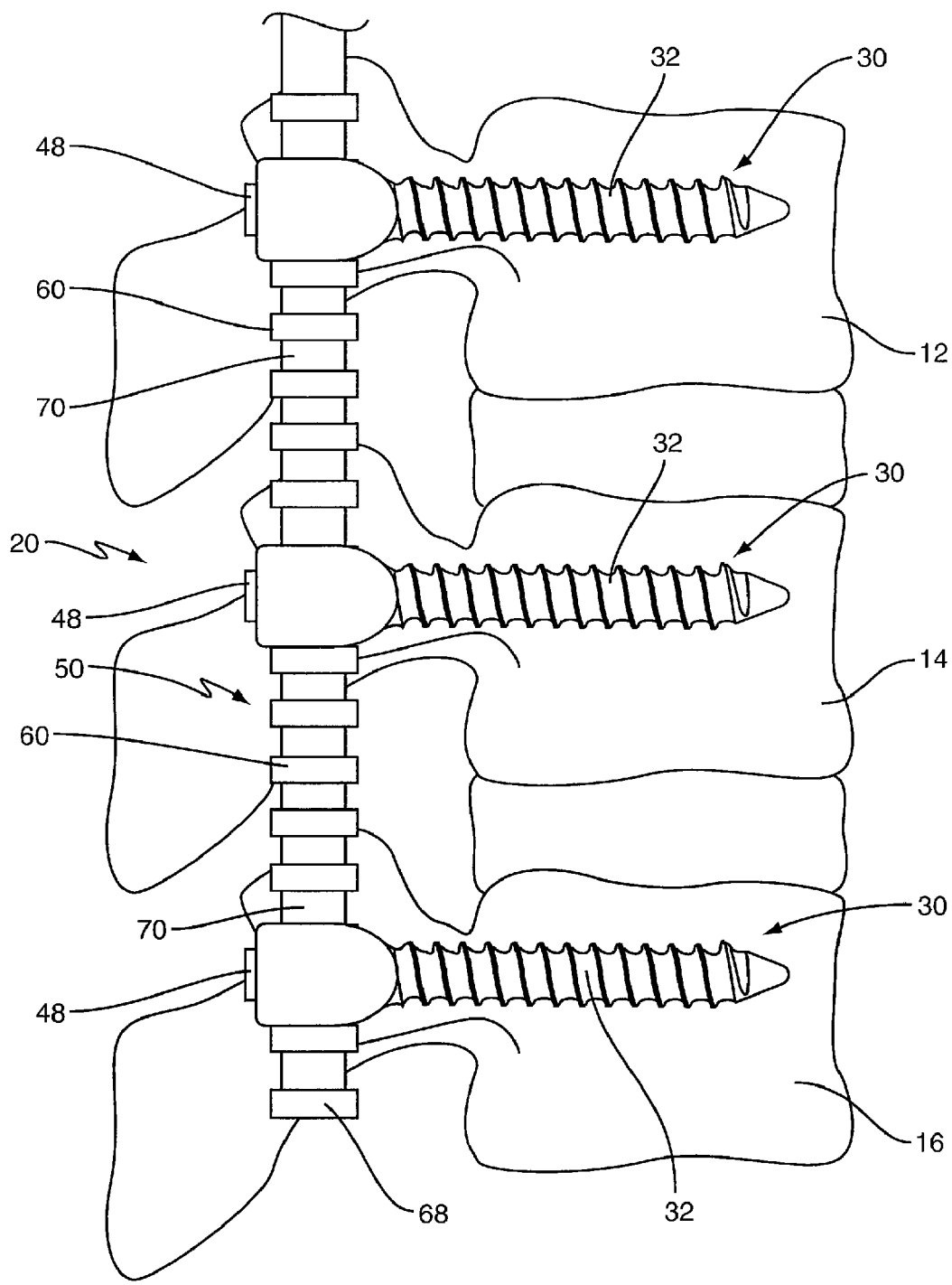
FIG. 11 shows an alternative embodiment of a dynamic spinal stabilization assembly being used to help stabilize multiple levels of a spinal column.

The discussion above has assumed that the dynamic spinal stabilization assembly 20 was being used to dynamically stabilize only two adjacent vertebral levels; however, it should be understood that the dynamic spinal stabilization assembly 20 could be used to stabilize three or more levels. For example, the dynamic spinal stabilization assembly 20 of FIG. 11 is used to dynamically stabilize a superior vertebra 12, an inferior vertebra 16, and an intermediate vertebra 14.

Finally, as discussed above, the dynamic spinal stabilization assembly 20 may include a variety of bone anchoring elements 30, including monoaxial and polyaxial bone screws. When used with polyaxial bone screws, care should be taken to ensure that the spacing of the collars 60 allows the polyaxial motion to be locked down, if desired. Further, for some embodiments, it may be desirable for the polyaxial bone screw to include the press plates or similar structures discussed above so that the clamping force for holding the rod assembly 50 may be transmitted, where appropriate, to the polyaxial locking mechanism.

The present invention may be carried out in other specific ways than those herein set forth without departing from the scope and essential characteristics of the invention. Further, the various aspects of the disclosed device and method may be used alone or in any combination, as is desired. The disclosed embodiments are, therefore, to be considered in all respects as illustrative and not restrictive, and all changes coming within the meaning and equivalency range of the appended claims are intended to be embraced therein.

What is claimed is:

1. An assembly for dynamic stabilization of a spine, comprising:
   a first bone anchoring element having a first bone engaging section extending along a first axis and a first coupling section, the first coupling section including a base section and two upstanding arms extending from said base section and having a first longitudinal channel defined between the upstanding arms and of at least a first length extending generally transverse to the first axis;
   a second bone anchoring element spaced from the first bone anchoring element;
   an elongate rod;
   an elastomeric sleeve disposed around said rod, the sleeve comprising a plurality of spaced apart recesses extending substantially parallel to the first axis;

a plurality of mounting collars each being positioned in one of the recesses such that an inner surface of the mounting collar engages an outer surface of the sleeve; and a locking member engageable with said upstanding arms and said rod, wherein the rod is slidably mountable to the first bone anchoring element via at least two of said collars and the rod is supported by the second bone anchoring element, and wherein the rod remains slidably mountable until said locking member is engaged with said sleeve or at least one of the mounting collars.

2. The assembly of claim 1 wherein the second bone anchoring element comprises a second bone engaging section extending along a second axis and a second coupling section, the second coupling section including a base section and two upstanding arms extending from said base section and having a second longitudinal channel defined between said upstanding arms and of at least the first length extending generally transverse to the second axis, the rod slidably mounted to the second bone anchoring element via at least another two of the collars.

3. The assembly of claim 2 further comprising a third bone anchoring element having a third bone engaging section and a third coupling section, wherein rod is slidably mounted to the third bone anchoring element via at least two of the collars.

4. The assembly of claim 1 further comprising a plurality of elastic elements each positioned in one of the recesses such that an inner surface of the elastic element engages the outer surface of the sleeve.

5. The assembly of claim 4 wherein the elastic elements and the collars alternate between adjacent recesses.

6. The assembly of claim 3 wherein elastomeric sleeve substantially longitudinally covers the rod.

7. The assembly of claim 1 wherein the locking element directly engages the at least two collars.

8. The assembly of claim 1 wherein the collars are spaced from one another by a distance not exceeding one-half the first length.

9. The assembly of claim 1 wherein the second bone anchoring element directly engages the rod.

10. The assembly of claim 1 wherein the rod is composed of a member of the group comprising titanium, PEEK, polyurethane, polypropylene, or polyethylene.

11. The assembly of claim 1 wherein the inner surface of the mounting collars comprises alignment features engaging the elastomeric sleeve.

12. An assembly for dynamic stabilization of a spine, comprising:

a first bone anchoring element having a first threaded shank section extending along a first axis and a first coupling section, the first coupling section including a base section and two upstanding arms extending from said base section and having a first longitudinal channel defined between said upstanding arms and of a first length extending generally transverse to the first axis;

a second bone anchoring element spaced from the first bone anchoring element;

an elongate rod;

an elastomeric sleeve disposed around said rod, the sleeve comprising a plurality of spaced apart recesses extending substantially parallel to the first axis;

a plurality of mounting collars each being positioned in one of the recesses such that an inner surface of the mounting collar engages an outer surface of the sleeve;

a locking member engageable with said upstanding arms and said rod, wherein the rod is slidably mountable to the first bone anchoring element via at least two of said collars and the rod is supported by the second bone anchoring element, wherein the elastomeric sleeve comprises a generally cylindrical body having a bore therethrough, the rod disposed in the bore, the rod slidably mounted to the first bone anchoring element via at least two of the collars and is supported by the second bone anchoring element, and wherein the rod remains slidably mountable until said locking member is engaged with said sleeve or at least one of the mounting collars.

13. The assembly of claim 12 wherein the second bone anchoring element comprises a threaded second shank section extending along a second axis and a second coupling section, the second coupling section having a second longitudinal channel defined between said upstanding arms and of at least the first length extending generally transverse to the second axis, and wherein the rod slidably mounts to the second bone anchoring element via at least another two of the collars.

14. The assembly of claim 1 further comprising a third bone anchoring element disposed in spaced relation to both of the first and second bone anchoring elements, the rod supported by the third bone anchoring element.

15. A method of dynamically stabilizing spinal column, comprising:

anchoring a first bone anchoring element to a first vertebra, the first bone anchoring element having a first bone engaging section and a first coupling section, the first coupling section including a base section and two upstanding arms extending from said base section;

anchoring a second bone anchoring element to a second vertebra;

providing an elongate rod having an elastomeric sleeve disposed about the rod, the sleeve comprising a plurality of spaced apart recesses extending substantially parallel to the rod;

providing a plurality of collars positioned in one of the recesses of the elastomeric sleeve such that an inner surface of the collar is engaged to an outer surface of the sleeve;

slidably mounting the rod to the first bone anchoring element by engaging at least two of the collars with the first coupling section;

mounting the rod to the second bone anchoring element; and engaging a locking member with said first bone anchoring element and said sleeve or at lease one of said mounting collars thus preventing the rod from further sliding movement.

16. The method of claim 3 wherein the mounting the rod to the second bone anchoring element comprises slidably mounting the rod to the second bone anchoring element by engaging at least two of the collars with the second bone anchoring element.

17. The method of claim 15, further comprising compressing at least one of the protrusions.

18. The method of claim 15 wherein the elastomeric sleeve substantially longitudinally covers the rod.

19. The method of claim 15 wherein the locking element directly engages the at least two collars.

20. The method of claim 15 further comprising a third bone anchoring element disposed in spaced relation to both of the first and second bone anchoring elements, the rod supported by the third bone anchoring element.

* * * * *